(12) United States Patent
Simpson et al.

(10) Patent No.: US 7,250,038 B2
(45) Date of Patent: Jul. 31, 2007

(54) FIXED NEEDLE SYRINGE WITH PROTECTIVE NEEDLE HOUSING

(75) Inventors: Roddi James Simpson, Watchung, NJ (US); Steven Huu Nguyen, Somerset, NJ (US)

(73) Assignee: Smiths Medical ASD, Inc., Keene, NH (US)

( * ) Notice: Subject to any disclaimer, the term of this patent is extended or adjusted under 35 U.S.C. 154(b) by 80 days.

(21) Appl. No.: 10/657,171

(22) Filed: Sep. 9, 2003

(65) Prior Publication Data

US 2005/0054986 A1  Mar. 10, 2005

(51) Int. Cl.
*A61M 5/32* (2006.01)
*A61M 5/00* (2006.01)

(52) U.S. Cl. .................. 604/192; 604/110; 604/198

(58) Field of Classification Search ............ 604/110, 604/187, 192, 197, 218, 263, 198; 128/919
See application file for complete search history.

(56) References Cited

U.S. PATENT DOCUMENTS

| | | | |
|---|---|---|---|
| 4,982,842 A | 1/1991 | Hollister | |
| 5,139,489 A * | 8/1992 | Hollister | 604/192 |
| 5,154,285 A | 10/1992 | Hollister | |
| 5,232,454 A | 8/1993 | Hollister | |
| 5,277,311 A | 1/1994 | Hollister | |
| 5,423,765 A | 6/1995 | Hollister | |
| 5,599,318 A * | 2/1997 | Sweeney et al. | 604/263 |
| 5,643,219 A * | 7/1997 | Burns | 604/192 |
| 5,681,295 A * | 10/1997 | Gyure et al. | 604/263 |
| RE37,110 E | 3/2001 | Hollister | |
| RE37,252 E | 7/2001 | Hollister | |
| 6,328,713 B1 | 12/2001 | Hollister | |
| 6,334,857 B1 | 1/2002 | Hollister | |
| 6,582,397 B2 | 6/2003 | Alesi et al. | |
| 7,029,461 B2 * | 4/2006 | Ferguson et al. | 604/198 |

OTHER PUBLICATIONS

Terumo SurGuard Safety Insulin Syringe, Terumo Medical Corporation, Jan. 2005.

* cited by examiner

*Primary Examiner*—Kevin C. Sirmons
*Assistant Examiner*—Elizabeth MacNeill
(74) *Attorney, Agent, or Firm*—Louis Woo

(57) ABSTRACT

A fixed needle syringe has a syringe barrel with its distal portion modified to accept a needle protective housing. In particular, the distal portion is formed with the a groove dimensioned to accept a collar that is attached to the housing. The inside surface of the collar is provided with a number of flanges that fit within the groove formed at the distal portion of the syringe barrel of the fixed needle syringe. Protrusions are provided at the inside surface of the collar to frictionally act against the syringe barrel, so that the needle protective housing does not freely rotate, but is rotatable relative to the syringe barrel by the application of a predetermined torque to either the collar or the housing attached thereto. An internal hook is provided in the housing to grasp the needle of the syringe, when the housing is pivoted to cover the needle extending from the needle hub of the syringe. Coacting locking members are provided at the base of the housing and the outside of the collar for fixedly retaining the housing relative to the collar, once the housing has been pivoted along the alignment position of the syringe. The collar reception portion of the syringe barrel may also be modified with a circumferential boss, with the inside surface of the collar correspondingly grooved so that the collar is matable with the syringe body in an alternative embodiment.

20 Claims, 2 Drawing Sheets

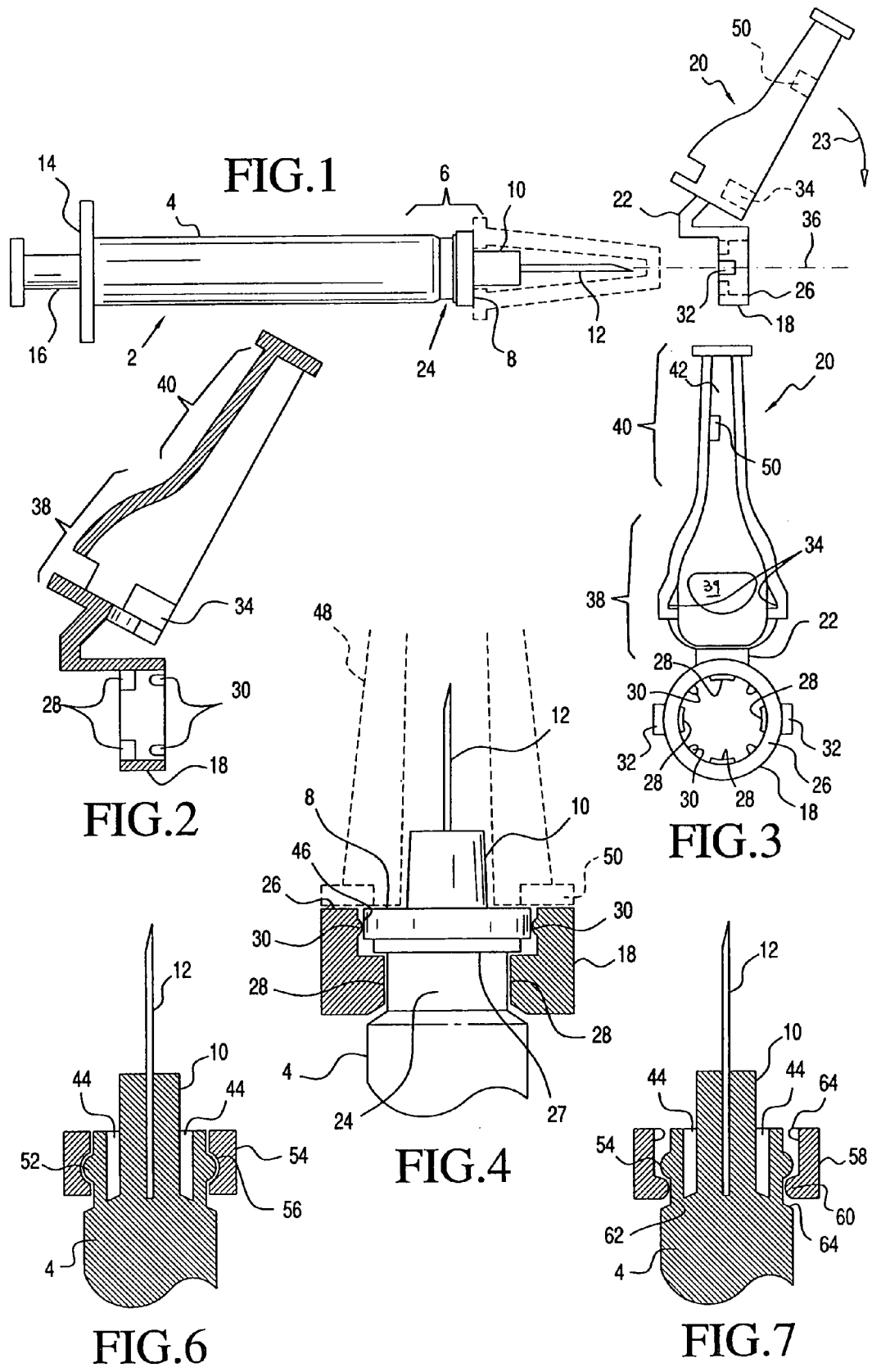

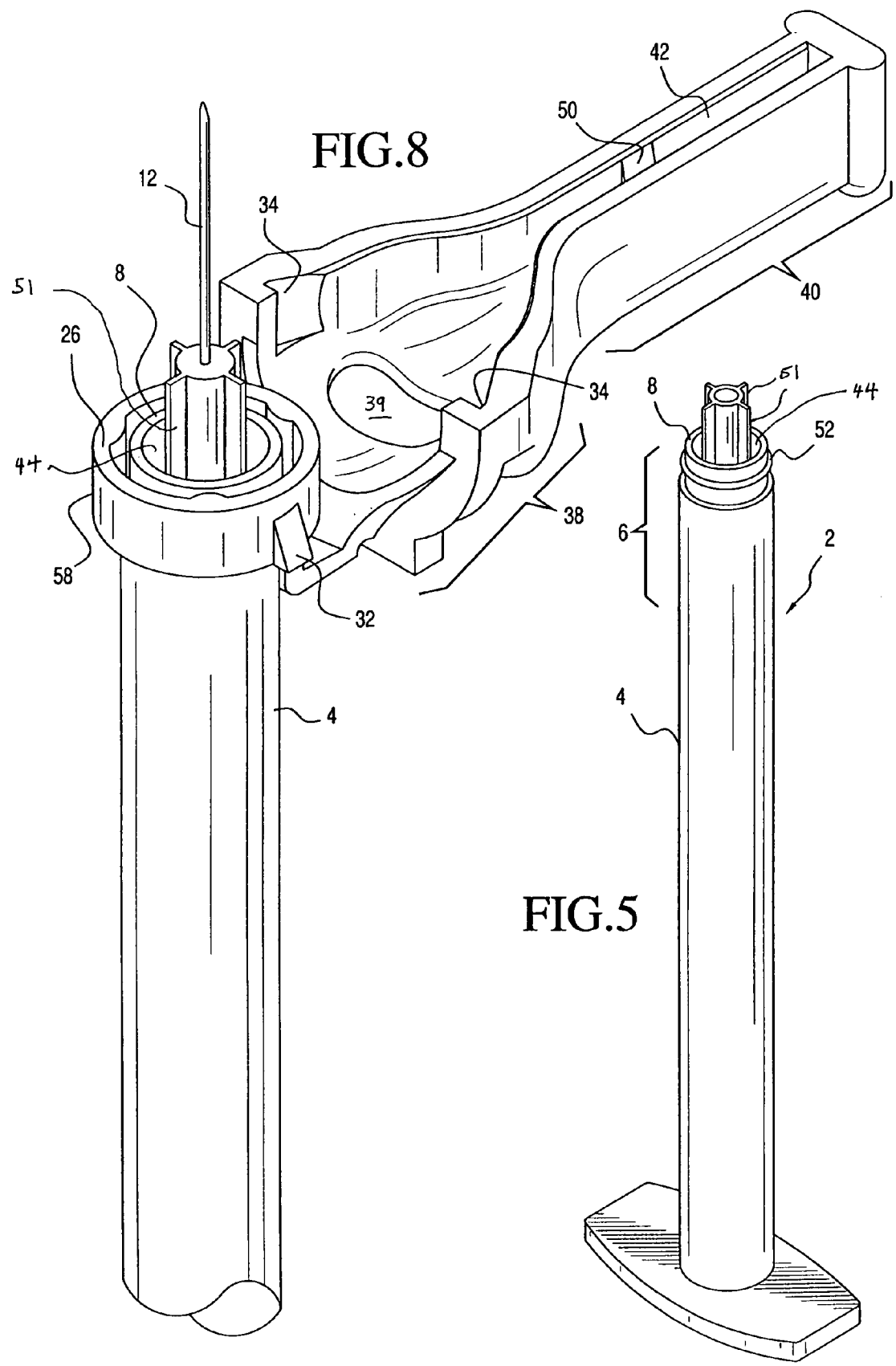

FIXED NEEDLE SYRINGE WITH PROTECTIVE NEEDLE HOUSING

FIELD OF THE INVENTION

The present invention relates to a fixed needle syringe and more particularly a fixed needle syringe that has a needle protection housing movably coupled to the syringe barrel of the syringe for enclosing the needle after use.

BACKGROUND OF THE INVENTION

The Assignee of the instant invention has assigned thereto a number of U.S. patents relating to the enclosure of a contaminated needle. The protective devices covered by these patents include an adapter housing that may be used with conventional syringes, a syringe with a fixed housing, Vacutainer holders equipped with a needle protection housing, and ways for fixedly retaining the protective housing over the contaminated needle after use. Without limitations, these patents include: U.S. Pat. Nos. 4,982,842; 5,139,489; 5,232,454; 5,154,285; 5,277,311; 5,423,765; RE37,110; RE37,252; U.S. Pat. Nos. 6,328,713; 6,334,857; and 6,582,397. The respective disclosures of the above noted patents are incorporated by reference herein.

The above patents do not deal with needle syringes that has a needle fixed thereto, for example a fixed needle insulin syringe.

SUMMARY OF THE PRESENT INVENTION

To provide a needle protection housing to a fixed needle syringe, a collar reception mechanism in the form of either a groove or a circumferential boss is formed at the distal portion of the syringe barrel of the fixed needle syringe. The collar reception mechanism is configured to accept a collar to which a needle protection housing is flexibly or pivotally attached. The inside circumference of the collar, depending on the type of collar reception mechanism formed at the distal portion of the syringe barrel, could have either internal flanges or is circumferentially notched. The medical plastic materials used for the manufacture of the fixed needle syringe and the collar are such that the collar may be elastically press-fitted to the syringe barrel by the application of a predetermined force. such plastic materials including for example p.v.c., polypropylene, polycarbonate, or any other appropriate plastic material. Once fitted to the syringe barrel, the collar will remain fixed thereat, albeit rotatable about the syringe barrel. Protuberances may be formed at the internal surface of the collar to provide friction or tension between the collar and the syringe barrel, so that the collar is rotatable about the syringe barrel only when a given torque is applied either to the housing or the collar, relative to the syringe barrel.

The needle protection housing is connected to the collar in such a way that when the collar is fitted to the syringe barrel, to envelop the needle fixedly extending from the needle hub of the syringe, the user only needs to pivot the protective housing to be in substantial alignment along the longitudinal axis of the syringe. The housing is configured such that its proximal portion, which is semi-circular in shape, would cover the needle hub while its distal portion, which is channel shaped, would cover the needle. To ensure that the contaminated needle is fixedly retained within the housing, a catch member such as for example a hook may be integrated in the housing for snap fitting over the needle, once the housing is pivoted to the position in alignment along the longitudinal axis of the syringe. As an alternative of, or to provide additional safety, coacting locking mechanisms may be provided at the base of the housing and the outer surface of the collar for anchoring the housing to the collar. Either the coacting mechanisms or the internal hook, or both, could be utilized in the instant invention fixed needle syringe.

For shipping purposes and before use, to maintain the sterility of the needle extending from the needle hub of the syringe, a needle sheath or cap is fitted to the needle hub for covering the needle. The collar of the needle protective housing, when properly fitted to the distal portion of the syringe barrel, provides a rest stop, per its top surface, for the needle sheath.

BRIEF DESCRIPTION OF THE FIGURES

The present invention will become apparent and the invention itself will be best understood by reference to the following description of the present invention taken in conjunction with the accompanying drawings, wherein:

FIG. 1 is a side view of a fixed needle syringe with its syringe barrel modified to receive the collar of a protective needle housing;

FIG. 2 is a sectional view of the protective needle housing shown in FIG. 1;

FIG. 3 is a front view of the needle protective housing;

FIG. 4 is a semi cut-away cross-sectional view showing the mating of the collar of the needle protection housing shown in FIG. 1 to the collar reception groove at the distal portion of the fixed needle syringe;

FIG. 5 is a perspective view of a fixed needle syringe, with the needle removed for ease of illustration, showing an alternative collar reception mechanism provided at the distal end of the syringe body;

FIG. 6 is a cross-sectional view of the alternative embodiment in which a collar with an internal groove is mated to the distal end of the syringe body of the needle syringe shown in FIG. 5;

FIG. 7 is a cross-section view of yet another embodiment in which the needle syringe of FIG. 5 is fitted with a different collar; and FIG. 8 is a perspective view of a fixed needle syringe fitted with a needle protection housing of the instant invention.

DETAILED DESCRIPTION OF THE INVENTION

With reference to FIGS. 1-4, the fixed needle safety syringe of the instant invention is shown to include a fixed needle syringe 2 that has a syringe barrel body 4 which includes a distal portion 6. Extending from the distal end 8 of the syringe barrel 4 is a needle hub 10, with a needle 12 fixedly extending therefrom. Syringe 2 further has a proximal end 14. As is well known, syringe 2 has a through bore (not shown) into which a plunger 16 is inserted by way of an opening provided at proximal end 14.

For the embodiment of the fixed needle syringe shown in FIG. 1, modification is effected at distal portion 6 at the syringe barrel 4 to enable the syringe barrel to be fitted thereto a collar 18 of a needle protective housing 20, which is connected to collar 18 by a living hinge 22. Thus connected, housing 20 is pivotable toward collar 18 per directional arrow 23.

For the modification of syringe barrel 4 for the embodiment shown in FIG. 1, a groove 24 is formed at distal portion 6 a predetermined distance from distal end 8. The location of groove 24 formed at syringe barrel 4 is designed such that when collar 18 is fitted thereto, the top surface 26 of collar 18 is substantially flushed with the shoulder or distal end 8 of syringe barrel 4. As best shown in FIG. 4, groove 24 is formed to include an undercut 27 that has a diameter slightly larger than groove 24.

Collar 18, as best shown in FIGS. 2 and 3, has a number of flanges 28 formed at its inner circumferential surface, at its proximal portion. A number of protrusions 30 are also formed at the inner surface of collar 18 but at its distal portion. Formed at the outer surface, at opposite sides of collar 18, are two extensions 32, each of which coacts with a corresponding catch 34 formed at the base of housing 20, when housing 20 is pivoted in the direction as indicated by directional arrow 23 to align along longitudinal axis 36 of collar 18. It should be noted that axis 36 is also the longitudinal axis of fixed needle syringe 2.

Housing 20 has a proximal portion 38 and a distal portion 40. Proximal portion 38 is semi-circular in shape, and has a dimension that enables it to cover needle hub 10, when collar 18 has been press fitted to groove 24 and housing 20 pivoted to cover needle 12. Proximal portion 38 has an opening 39 at its back wall that allows the side of collar 18 that is enclosed by proximal portion 38 to be viewed when hub 10 is covered by housing 20. A perspective view of the opening provided by the semi-circular configuration of proximal portion 38 of needle housing 20 is shown in FIG. 8. Distal portion 40 of housing 20 extends from proximal portion 38 in the form of a narrow channel 42. Channel 42 is formed by an open slot through which needle 12 passes when housing 20 is pivoted towards the longitudinal axis 36 for covering needle 12. As shown in FIG. 3, the slot into channel 42 extends to the opening that forms the semi-circular configuration of proximal portion 38 of housing 20.

With reference to FIG. 4, collar 18 is shown to have been press fitted to the collar reception groove 24 at the distal portion 6 of syringe barrel 4. As shown, flanges 28 are matingly fitted to groove 24. The dimension of the inside diameter and more particularly the circumference formed by flanges 28 is such that it is slightly larger than the diameter of groove 24, so that collar 18 is rotatable about groove 24, after collar 18 is press fitted thereto. Collar 18 is fittable to groove 24 because of the elastic characteristics of the aforenoted conventional medical plastics from which collar 18, housing 20 and syringe barrel 4 are formed. Also, with reference to FIGS. 5 to 8, note that there is a circumferential or annular space 44 formed between distal end 8 and the portion of hub 10 that extends from distal portion 6 of syringe barrel 4. Annular space 44 therefore surrounds at least one portion of needle hub 10 so that when collar 18 is forced fitted onto syringe barrel 4, the distal end 8 would slightly compress while at the same time collar 18 would slightly expand, so that with the appropriate pressing force, collar 18 is matingly fitted to the collar reception portion of the syringe barrel 4. Annular space 44 thus facilitates the mating of collar 18 to the collar reception portion of syringe barrel 4.

For the embodiment of FIG. 1, to prevent free rotation of collar 8 relative to syringe barrel 4, bumps or protrusions 30 provided at the inner surface of the distal portion of collar 18 are designed to be in contact with area 46 of syringe barrel 4. The tension applied by protrusions 30 against area 46 is such that collar 18, although not freely rotatable, is nonetheless rotatable relative to syringe barrel 4, if a predetermined torque is applied against either collar 18, or housing 20 attached thereto for rotating collar 18.

Further with respect to FIG. 4, note that needle 12, before use, is covered by a needle cap or needle sheath 48, shown in dashed lines. See also FIG. 1. Needle sheath 48 ensures the sterility of needle 12 prior to use.

As best shown in FIG. 8, note that with collar 18 fitted to collar reception area 24 of syringe barrel 4, the top surface 26 of collar 18 becomes substantially flushed with or in a substantially planar relationship with the shoulder or distal end 8 of syringe barrel 4, to thereby provide a rest stop for base 50 of needle sheath 48.

In operation, needle sheath 48 is removed from needle hub 10. After use, to cover the now contaminated needle 12, housing 20 is pivoted in the direction as shown per directional arrow 23 until it becomes substantially aligned along longitudinal axis 36. At about that time, needle 12 snaps past and is grasped by integral catch member 50, which may be in the form of a hook, within channel 42 of housing 20; and hub 10 is covered by proximal portion 38 of housing 20. Also, extensions 32 formed on the outside of collar 18 become caught by catches 34 formed at the base of housing 20. As a result, needle 12 is fixedly retaining within housing 20 and housing 20 in turn is fixedly retained to collar 18, with collar 18 not removable from syringe barrel 4 due to flanges 28 having a small diameter than undercut 27 of groove 24. The now used fixed needle syringe, with the contaminated needle no longer exposed, can then be disposed of.

FIG. 5 shows an alternative embodiment of the fixed needle syringe of the instant invention. For this embodiment, note that the needle reception area of syringe barrel 4, instead of a groove, has a boss 52 formed circumferentially at distal portion 6. Note further that hub 10 has a number of evenly spaced fins 51 extending lengthwise along the hub. For the sake of simplicity, the needle of the fixed needle syringe is not shown in the FIG. 5 embodiment. For mating with the alternative syringe of FIG. 5, a collar 54 as shown in FIG. 6 may be utilized. For the alternative embodiments, components that are the same as in the FIG. 1 embodiment are labeled the same.

As for collar 54, note that it has an internal groove or notch 56 formed circumferentially along its inner surface so that when collar 54 is fitted to the distal portion of syringe barrel 4, notch 56 will snap over and become mated to boss 52 of the syringe barrel. The dimension of collar 54, particularly that of notch 56, is designed such that collar 54 is rotatable relative to syringe barrel 4, but is not freely rotatable thereabout.

Yet another embodiment of the collar of the instant invention is shown in FIG. 7. There, instead of an internal groove 56 as shown in the FIG. 6 embodiment, collar 58 has a plurality of extensions, or flanges 60, provided at its proximal portion. Flanges 60 are fitted within the groove 62 formed by the lower portion of boss 54 and surface 64 of syringe barrel 4. For the embodiment of FIG. 7, collar 58 is manufactured so that flanges 60 would have a dimension that would allow them to contact groove 62 so as not to be freely rotatable and yet rotatable with the application of a predetermined torque to either collar 58 or the housing attached thereto. Protrusions 64 may be provided at the distal portion of ring collar 58 to apply the appropriate rotation free friction or tension relative to syringe barrel 4.

FIG. 8 is a perspective view of the fixed needle syringe of the instant invention with the needle sheath having been removed to expose needle 12. The collar shown mated to syringe barrel 4 is the collar 58 shown in the FIG. 7 embodiment.

The invention claimed is:

1. Safety apparatus, comprising:
a unitary molded syringe having a syringe barrel, said syringe barrel having a distal portion and a distal end, a needle hub integrally mounted on said distal portion, a needle extending from said needle hub, a portion of said needle hub being circumferentially separated from said distal end by an annular space, a collar reception mechanism formed at said distal portion proximate to said distal end of said syringe barrel, a collar having a housing for protecting said needle pivotally attached thereto matingly fitted to said collar reception mechanism by first passing said distal end, said annular space enabling said distal end to compress toward said needle hub to facilitate the fitting of said collar to said collar reception mechanism when said collar makes contact therewith, said housing pivotable to a position along the longitudinal axis of said syringe, said housing having a slot wherethrough said needle passes when said housing is pivoted to said position for covering said needle.

2. Safety apparatus of claim 1, wherein said collar reception mechanism comprises a groove formed circumferentially about said distal portion, and wherein said collar has a diameter slightly larger than said groove so that said collar is rotatable about said groove once said collar is mated to said groove, said collar having at least one protrusion at its inside surface that contacts the surface of said syringe barrel with sufficient tension to prevent free rotation of said collar relative to said syringe barrel.

3. Safety apparatus of claim 1, further comprising at least one locking portion provided at a base of said housing, and at least an other locking portion provided at the outside circumference of said collar, wherein said one and other locking portions coact with each other to fixedly retain said housing relative to said collar when said housing is pivoted to be in alignment along said longitudinal axis of said syringe to cover said needle.

4. Safety apparatus of claim 1, further comprising a catch member within said housing for fixedly retaining said needle within said housing when said housing is pivoted along said longitudinal axis of said syringe to cover said needle.

5. Safety apparatus of claim 1, wherein said collar reception mechanism comprises a groove formed circumferentially about said distal portion, and wherein said collar comprises a plurality of flanges at its inside surface, said flanges preventing said collar from being removed from said syringe barrel once said collar is fitted to said groove.

6. Safety apparatus of claim 1, wherein said collar reception mechanism comprises a groove formed circumferentially about said distal portion, and wherein said collar has a top surface, the top surface being flush with the distal end of said syringe barrel when said collar is fitted to said groove, said apparatus further comprising a needle sheath for covering said needle before use, said sheath having an open end whereinto said needle is inserted when said sheath is fitted to said needle hub, the top surface of said collar providing a stop for said sheath when said sheath is fitted to said needle hub to cover said needle.

7. Safety apparatus of claim 1, wherein said needle protection housing comprises a proximal portion and a distal portion, said proximal portion having a base connected by a living hinge to said collar, said proximal portion being semi-circular and having a dimension sufficient to cover said needle hub, said distal portion of said needle protection housing extending from said proximal portion to form a channel for covering said needle with said slot forming the opening through which said needle passes into said channel when said housing is pivoted to be in alignment along said longitudinal axis to cover said needle, an opening provided at the back wall of said proximal portion away from said slot.

8. Safety apparatus of claim 1, further comprising a sheath fitted to the needle hub to cover the needle prior to the needle being used so as to ensure that the needle stays sterile prior to use.

9. Safety apparatus of claim 1, wherein said needle hub comprises at least one fin extending along said hub.

10. A safety syringe comprising: a unitary molded syringe barrel having a proximal end whereinto a plunger is movably inserted, a distal portion and a distal end, a needle hub having a smaller circumference than said syringe barrel integrally extending from said distal portion, a portion of said needle hub being circumferentially separated from said distal end by an annular space, a needle fixedly mounted on said needle hub, a sheath having an open end engaged to said hub for covering said needle, a collar reception mechanism formed at said distal portion proximate to said distal end of said syringe barrel, a collar having a housing for protecting said needle pivotally attached thereto matingly fitted to said collar reception mechanism by first passing said distal end, said annular space enabling said distal end to compress toward said needle hub to facilitate the fitting of said collar to said collar reception mechanism when said collar makes contact therewith, said housing pivotable to a position along the longitudinal axis of said syringe, said housing having a slot wherethrough said needle passes when said housing is pivoted to said position for covering said needle after the removal of said sheath from said hub.

11. Safety syringe of claim 10, wherein said collar reception mechanism comprises a groove, and wherein said collar is rotatable about said groove, said collar having friction means at its inside surface that contacts said syringe barrel to prevent said collar from rotating relative to said syringe barrel without a torque being applied against either said collar or said housing.

12. Safety syringe of claim 10, wherein said housing comprises a base and at least one locking portion provided at said base and wherein said collar comprises at least an other locking portion provided at its outside circumference, said one and other locking portions coacting with each other to fixedly retain said housing relative to said collar when said housing is pivoted to be in alignment along said longitudinal axis of said syringe to cover said needle.

13. Safety syringe of claim 10, wherein said housing comprises an integral catch member for fixedly retaining said needle within said housing when said housing is pivoted along said longitudinal axis of said syringe to cover said needle.

14. Safety syringe of claim 10, wherein said collar reception mechanism comprises a groove, and wherein said collar comprises a plurality of flanges at its inside surface, said flanges preventing said collar from being removed from said syringe barrel once said collar is snap fitted to said groove.

15. Safety syringe of claim 10, wherein said collar reception mechanism comprises a groove, and wherein said collar has a top surface, the top surface of said collar being flush with the distal end of said syringe barrel when said collar is fitted to said groove, the top surface of said collar providing a stop for said sheath when said sheath is engaged to said needle hub to cover said needle.

16. Safety syringe of claim 10, wherein said needle protection housing comprises a proximal portion and a distal portion, said proximal portion having a base connected by a living hinge to said collar, said proximal portion being semi-circular for covering said needle hub, said distal portion being a channel extending from said proximal portion with said slot forming the opening along said channel wherethrough said needle passes into said channel when said housing is pivoted to be in alignment along said longitudinal axis, an opening provided at the back wall of said proximal portion away from said slot.

17. Safety syringe of claim 10, wherein said needle hub comprises at least one fin extending along said hub.

18. A safety syringe comprising:
   a unitary molded syringe barrel having a proximal end whereinto a plunger is movably inserted, a distal portion and a circumferential wall that forms a distal end that is part of said distal portion, a needle hub having a smaller circumference than said syringe barrel integrally extending from said distal portion with at least one portion thereof surrounded by said distal end so that an annular space circumferentially separates said distal end and said needle hub, and a collar reception mechanism formed at said distal portion proximate to said distal end of said syringe barrel;
   a needle fixedly mounted on said needle hub;
   a sheath engaged to said hub for covering said needle prior to said needle being used;
   a collar movably fitted to said collar reception mechanism, said collar being mated to said collar reception mechanism by first passing said distal end, said annular space enabling said distal end to compress toward said needle hub to facilitate the mating of said collar to said collar reception mechanism when said collar makes contact therewith;
   a housing for protecting said needle pivotally attached to said collar, said housing pivotable to a position along the longitudinal axis of said needle, said housing having a slot wherethrough said needle passes when said housing is pivoted to said position for covering said needle after the removal of said sheath from said hub.

19. Syringe of claim 18, wherein said housing comprises a proximal portion and a distal portion, said proximal portion having an opening at its back wall away from said slot.

20. Safety syringe of claim 18, wherein said needle hub comprises at least one fin extending along said hub.

* * * * *